(12) United States Patent
Drasler et al.

(10) Patent No.: US 8,721,679 B2
(45) Date of Patent: May 13, 2014

(54) APPARATUS AND METHOD FOR CLOSING AN OPENING IN A BLOOD VESSEL USING A PERMANENT IMPLANT

(75) Inventors: William J. Drasler, Minnetonka, MN (US); Tracee Eidenschink, Wayzata, MN (US); Joseph M. Thielen, Buffalo, MN (US); Mark L. Jenson, Greenfield, MN (US); Anu Sadasiva, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 779 days.

(21) Appl. No.: 12/026,115

(22) Filed: Feb. 5, 2008

(65) Prior Publication Data

US 2008/0312684 A1 Dec. 18, 2008

Related U.S. Application Data

(60) Provisional application No. 60/888,219, filed on Feb. 5, 2007.

(51) Int. Cl.
*A61B 17/03* (2006.01)

(52) U.S. Cl.
USPC .................................................. 606/213

(58) Field of Classification Search
USPC ................. 606/151, 200, 213–217; 128/898; 623/23.72
See application file for complete search history.

(56) References Cited

U.S. PATENT DOCUMENTS

| 4,007,743 | A | * | 2/1977 | Blake | 606/213 |
|---|---|---|---|---|---|
| 5,334,217 | A | * | 8/1994 | Das | 606/213 |
| 5,425,744 | A | * | 6/1995 | Fagan et al. | 606/213 |
| 5,437,631 | A | * | 8/1995 | Janzen | 604/506 |
| 5,702,421 | A | | 12/1997 | Schneidt | |
| 6,174,322 | B1 | * | 1/2001 | Schneidt | 606/213 |
| 6,214,029 | B1 | * | 4/2001 | Thill et al. | 606/213 |
| 6,221,092 | B1 | * | 4/2001 | Koike et al. | 606/213 |
| 6,616,675 | B1 | | 9/2003 | Evard et al. | |
| 7,165,552 | B2 | * | 1/2007 | Deem et al. | 128/898 |
| 7,288,105 | B2 | * | 10/2007 | Oman et al. | 606/215 |
| 7,335,220 | B2 | * | 2/2008 | Khosravi et al. | 606/213 |
| 2003/0028213 | A1 | * | 2/2003 | Thill et al. | 606/200 |
| 2003/0144695 | A1 | | 7/2003 | McGuckin, Jr. et al. | |
| 2006/0190036 | A1 | | 8/2006 | Wendel et al. | |
| 2006/0224183 | A1 | | 10/2006 | Freudenthal | |
| 2006/0259074 | A1 | * | 11/2006 | Kelleher et al. | 606/213 |
| 2007/0225758 | A1 | | 9/2007 | Preinitz et al. | |

FOREIGN PATENT DOCUMENTS

| WO | 2007/025019 A2 | 3/2007 |
|---|---|---|
| WO | 2008/094691 A2 | 8/2008 |

* cited by examiner

*Primary Examiner* — Kathleen Holwerda
(74) *Attorney, Agent, or Firm* — Seager, Tufte & Wickhem LLC

(57) ABSTRACT

An apparatus and method for closing an arteriotomy site is disclosed. The apparatus includes inner and outer frames adapted to sandwich a blood vessel wall therebetween. The inner and outer frames may be manufactured from memory metals such that they can be compressed during the insertion into the tissue tract proximate the arteriotomy site, and then deployed into an expanded configuration larger than the dimensions of the arteriotomy opening itself. A universal joint connects the inner and outer frames to ensure proper pivoting therebetween. In addition, polymeric coverings can be provided on the inner and outer frames to ensure closure, while a collagen plug can also be provided between inner and outer frames to facilitate closure as well.

24 Claims, 6 Drawing Sheets

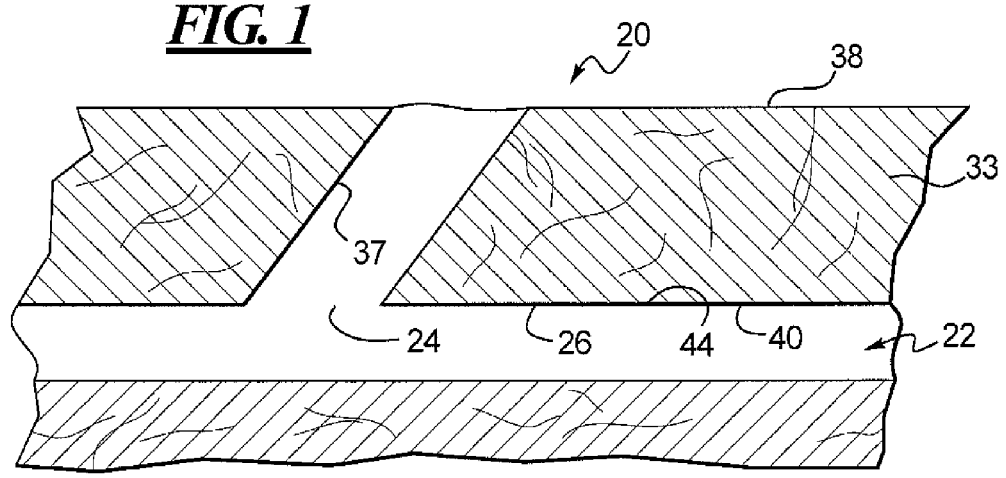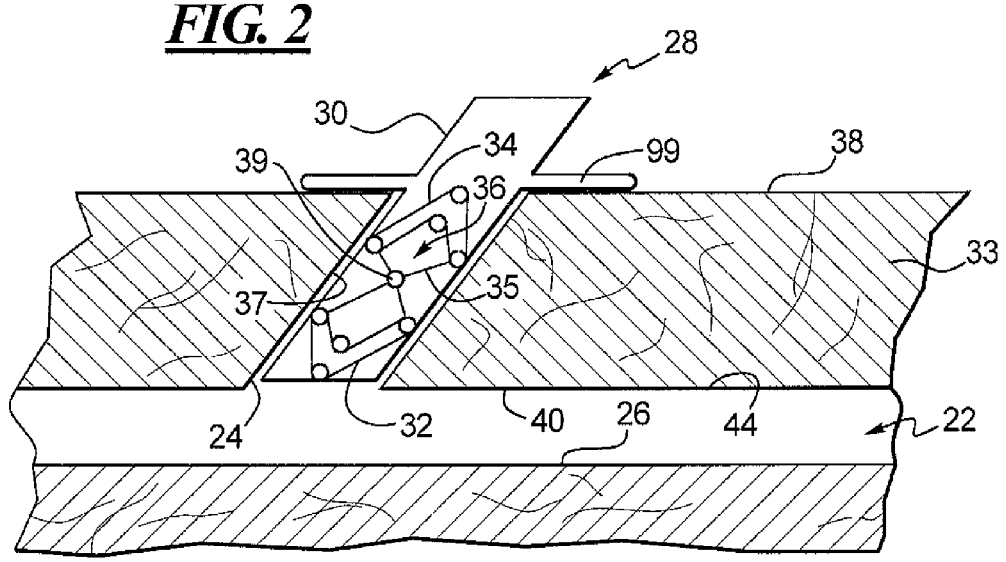

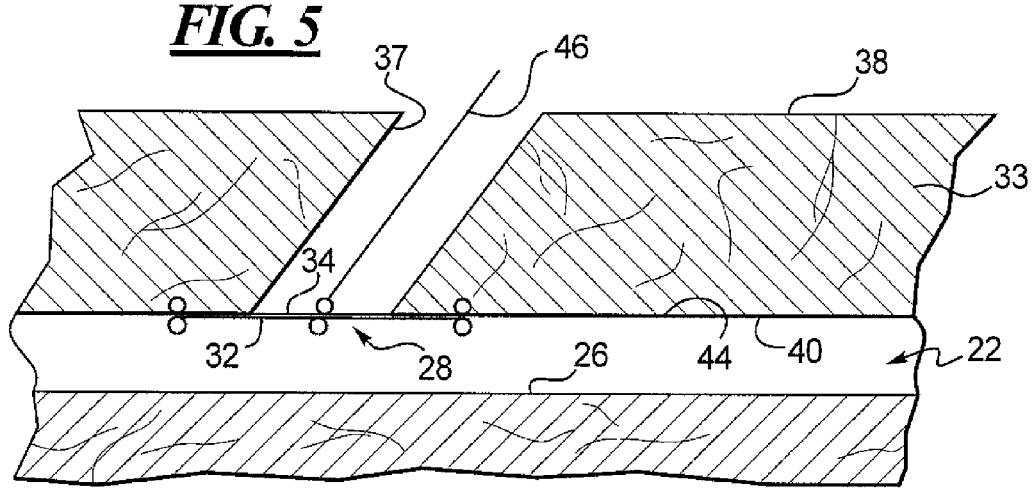
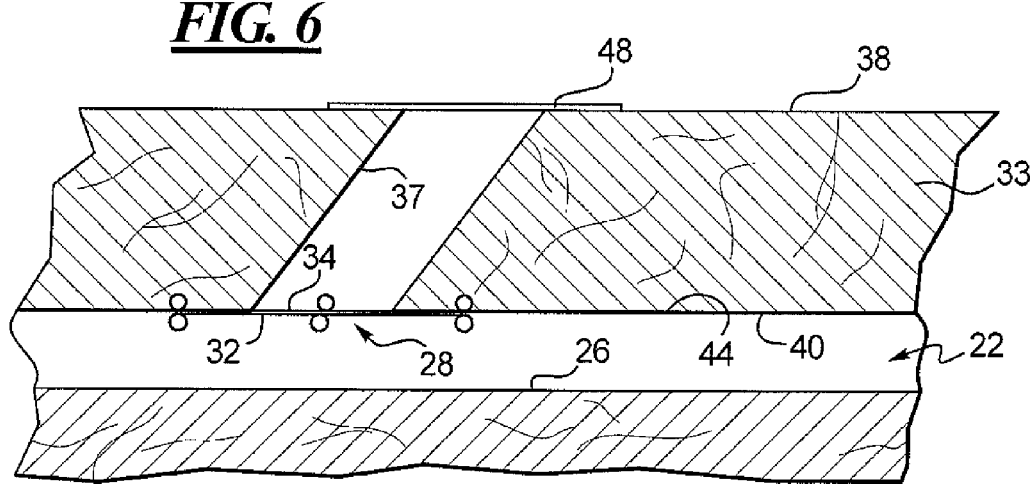

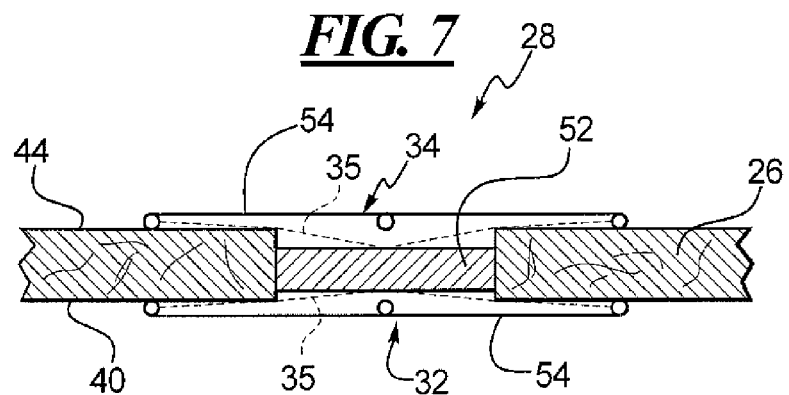
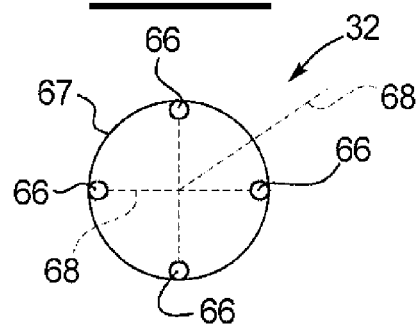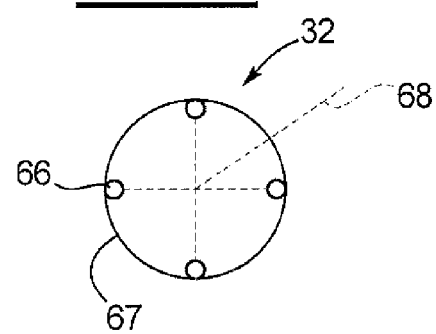
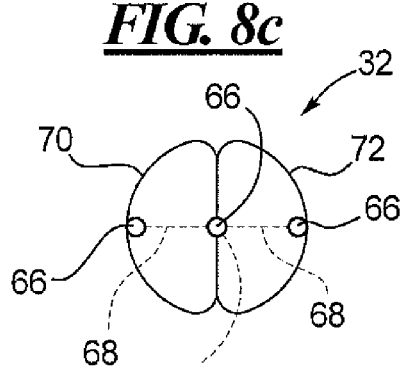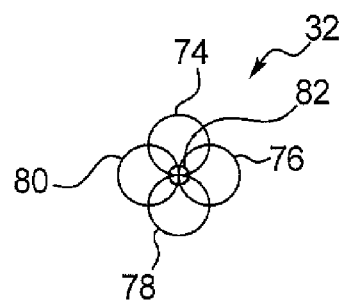

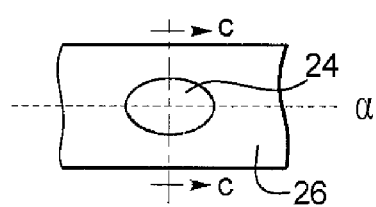 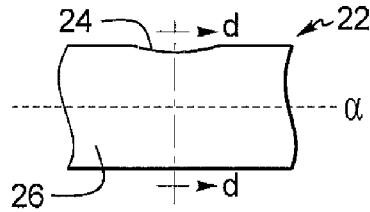
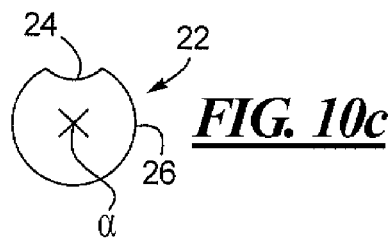 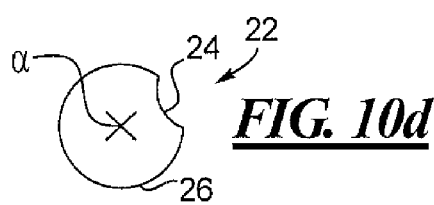
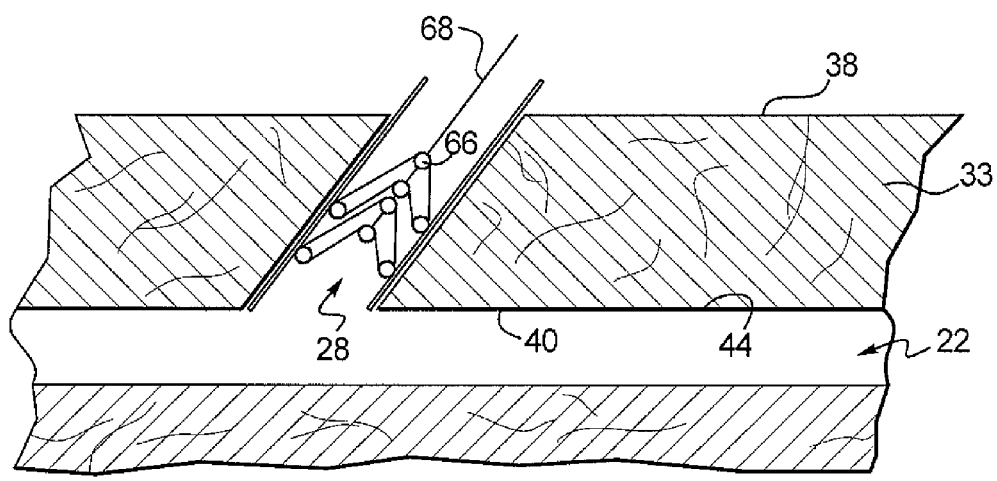

APPARATUS AND METHOD FOR CLOSING AN OPENING IN A BLOOD VESSEL USING A PERMANENT IMPLANT

CROSS-REFERENCE TO RELATED APPLICATION

This application is a non-provisional patent application claiming priority under 35 USC §119(e) to U.S. provisional patent application Ser. No. 60/888,219 filed on Feb. 5, 2007.

FIELD OF THE DISCLOSURE

The present disclosure generally relates to medical devices and, more particularly, relates to apparatus and methods for closing arteriotomy sites.

BACKGROUND OF THE DISCLOSURE

In many medical procedures, such as balloon angioplasty and the like, it is known how to create an opening in a blood vessel, known as an arteriotomy, to allow for the insertion of various medical devices which can be navigated through the blood vessel to the site to be treated. Typically, the opening is formed in the femoral artery at a point proximate the groin and a series of medical devices are inserted in sequence. For example, a guide wire may first be inserted through the tissue tract created between the skin or the epidermis of the patient down through the subcutaneous tissue and into the opening formed in the blood vessel. The guide wire is then navigated through the blood vessel to the site of the occlusion, the heart, or any other area to be treated. Once the guide wire is in place, an introducer sheath can be slid over the guide wire to form a wider, more easily accessible, tract between the epidermis and the opening into the blood vessel If an angioplasty needs to be performed, the balloon catheter can then be introduced over the guide wire again through the introducer sheath, through the opening in the femoral artery, and then up the blood vessel to the site of the occlusion.

Once the procedure is performed, the guide wire, balloon catheter and any other equipment introduced can be retracted through the blood vessel, out through the opening in the blood vessel wall, out through the introducer sheath, and out of the body entirely The introducer sheath can then be removed and the physician or other medical technician is presented with the challenge of trying to close the opening both in the femoral artery and the tissue tract formed in the epidermis and subcutaneous tissue Most importantly, the opening in the blood vessel must be closed as soon as possible.

Over the years that these procedures have been performed, a number of apparatus and methods have been created for closing the opening in the blood vessel. Traditionally, and still commonly today, the opening is closed simply by the application of manual pressure. If sufficient pressure is applied, the blood vessel is constricted until a clot or thrombus forms whereupon the pressure can be removed and eventually the patient can become ambulatory once again. However, a number of drawbacks are associated with such a method For one, the process is very time consuming often taking many hours for the thrombus to fully form, during which time the patient is required to be stationary In addition, the mere application of such significant pressure to the groin is often quite uncomfortable for the patient.

In light of these difficulties, a number of proposals have been introduced to potentially alleviate such drawbacks In one approach, an anchor is inserted through the tissue tract and the blood vessel with a filament extending therefrom and connected to a sealing plug by a pulley arrangement. Once the anchor engages an interior surface of the blood vessel the filament can be used to pull the sealing plug securely into the tissue tract. While this approach does more quickly close the opening in the blood vessel than manual pressure application, it also results in the unfavorable characteristic of leaving a foreign body in the patient after the procedure is completed.

Another approach uses a resistive heating coil inserted into the opening in the blood vessel. Upon energization of the heating coil, the blood in the vicinity of the opening is caused to coagulate given the rise in temperature. This can be accomplished in combination with the introduction of a procoagulant into the site to again expedite the creation of the coagulation. While this approach has also met with some level of success, it also results in the introduction of a foreign body and/or substance into the tissue of the patient.

A still further approach involves the introduction of a collagen plug into the site of the opening. Such a plug is sized to be frictionally engaged by the sides of the opening in the blood vessel and thus held in place until coagulation of blood forms around the collagen plug The collagen plug is biodegradable and eventually is dispersed into the blood flow and eliminated from the body. However, just the introduction of such a foreign substance into the body can sometimes be, at the very least, inflammatory and uncomfortable for the patient.

In one collagen plug approach, a balloon catheter is inserted into the blood vessel, inflated, and then pulled back against an interior surface of the blood vessel wall to serve as a backstop. The collagen plug in such an approach is shaped and sized as to closely match the opening in the blood vessel wall and is pushed down into the tissue tract until it engages the inflated balloon. The inflated balloon can then be deflated and withdrawn leaving the collagen plug in place.

In another collagen plug approach, a delivery sheath wider than the opening in the blood vessel wall is used and then a collagen plug corresponding to the size of the inner diameter of the delivery sheath is pushed through the sheath so as to engage the outer surface of the blood vessel wall. The plug can then be tamped or compressed down against the exterior surface of the blood vessel wall such that a portion of the collagen extends into the opening of the blood vessel wall.

While each of the foregoing approaches have been met with some level of success, it can be seen that each also has substantial drawbacks. Accordingly, it would be advantageous for the art to provide an apparatus and method which can quickly close the opening in the blood vessel wall, forms a thrombus which reliably remains in place after formation, and minimizes patient discomfort.

SUMMARY OF THE DISCLOSURE

In accordance with one aspect of the disclosure, an apparatus for closing an opening in a blood vessel is disclosed comprising a inner frame adapted to be positioned against an interior surface of the blood vessel wall, an outer frame adapted to be positioned against the exterior surface of the blood vessel wall, and a universal joint connecting the inner frame to the outer frame.

In accordance with another aspect of the disclosure, the method of closing an opening in a blood vessel is disclosed comprising insetting a delivery sheath through the tissue tract extending from an epidermal layer to an arteriotomy opening, wherein the delivery sheath includes an apparatus for closing the arteriotomy opening therein. The apparatus includes an inner frame and an outer frame connected by a universal joint with the inner and outer frames being held in a compressed configuration within the delivery sheath The method further includes extending the inner frame from the delivery sheath and into the blood vessel wherein the inner frame expands into a deployed configuration when extended from the delivery sheath The method further includes retracting the delivery sheath and apparatus a distance to engage the deployed inner frame against an interior surface of a blood vessel wall, and pulling the delivery sheath away from the outer frame with the outer frame expanding into a deployed configuration when the delivery sheath is pulled away, and the outer frame being in engagement with an outer surface of a blood vessel wall.

In accordance with another aspect of the disclosure, an apparatus for closing an opening in a blood vessel is disclosed comprising an inner frame, an outer frame, a universal joint, and a collagen plug. The inner frame is made of memory metal and is compressible into an insertion configuration and expandable into a deployed configuration. The inner frame has a width greater than the opening when deployed and a width smaller than the width of the opening when inserted. The inner frame includes a polymer cover connected thereto. The outer frame is made of memory metal and is compressible into an insertion configuration and expandable into a deployed configuration. The outer frame has a width greater than the width of the opening when deployed and a width smaller than the width of the opening when inserted. The outer frame includes a polymer cover connected thereto. A universal joint is connected to the inner and outer frames with the universal joint being made of a thread and allowing multi-directional pivoting between the inner and outer frames. The biodegradable plug is positioned between the inner and outer frames.

These and other aspects and features of the disclosure will become more apparent upon reading the following detailed description when taken in conjunction with the accompanying drawings.

BRIEF DESCRIPTION OF THE DRAWINGS

FIG. 1 is a cross-sectional view of an arteriotomy site showing a blood vessel, an opening in the blood vessel wall, and a tissue tract extending between the blood vessel and the epidermal layer of the patient;

FIG. 2 is a cross-sectional view similar to FIG. 1, but with the apparatus of the pending disclosure inserted into a delivery heath in the tissue tract;

FIG. 5 is a cross-sectional view similar to FIG. 4, but with the delivery sheath fully removed and the outer frame thereby fully deployed against an outer surface of the blood vessel wall;

FIG. 6 is a cross-sectional view similar to FIG. 5, but with the closure device fully deployed, a retraction thread removed and a bandage provided over the epidermal layer;

FIG. 7 is a enlarged cross-sectional view of an alternative embodiment of the apparatus shown in a deployed state with a collagen plug between the inner and outer frames;

FIG. 8a is a plan view of one embodiment of the inner frame in a circular configuration;

FIG. 8b is a plan view of an alternative embodiment of an inner frame having a lesser number of retraction coils than the embodiment of FIG. 8a;

FIG. 8c is a plan view of an alternative embodiment of an inner frame being split into two halves;

FIG. 8d is a plan view of an alternative embodiment of an inner frame in a cloverleaf configuration;

FIG. 10a is a top view of a blood vessel with a "top-stick" opening;

FIG. 10b is a top view of a blood vessel with a "side-stick" opening;

FIG. 10c is a sectional view of FIG. 10a taken along line c-c of FIG. 10a;

FIG. 10d is a sectional view of FIG. 10b taken along line d-d of FIG. 10b; and

FIG. 11 is a sectional view of the apparatus being removed after deployment.

Figure 3:
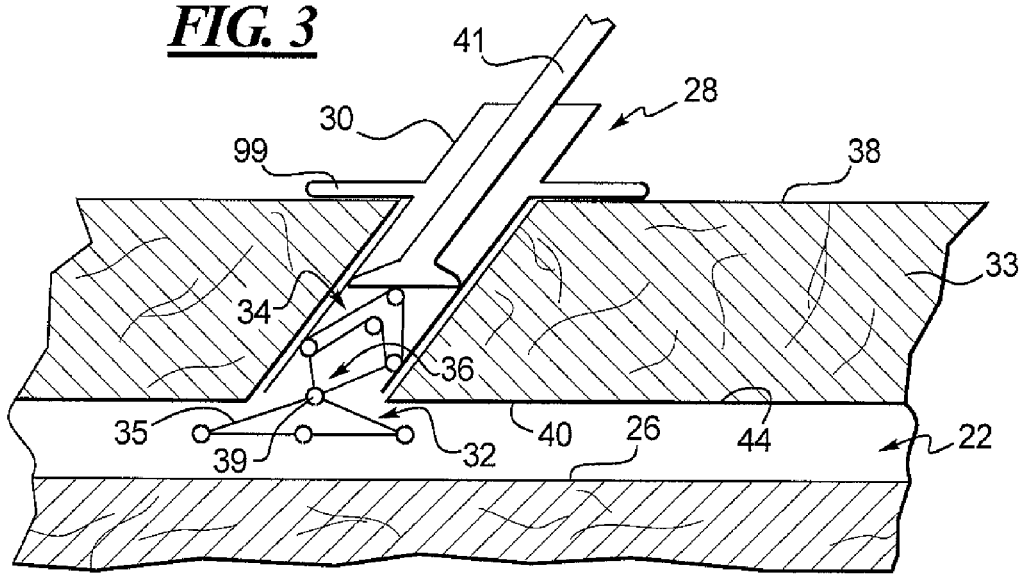
FIG. 3 is a cross-sectional view similar to FIG. 2, but with the inner frame of the apparatus deployed into the blood vessel.

While the present disclosure is susceptible to various modifications and alternative constructions, certain illustrative embodiments thereof have been shown in the drawings and will be described below in detail. It should be understood, however, that there is no intention to limit the present invention to the specific forms disclosed, but on the contrary, the intention is to cover all modifications, alternative constructions, and equivalents falling within the spirit and scope of the present invention.

DETAILED DESCRIPTION OF THE DISCLOSURE

Referring now to the drawings and with specific reference to FIG. 1, the site of an arteriotomy is referred to by reference numeral 20 and is the focus of the apparatus and method disclosed herein. As identified above, many modern medical procedures include the percutaneous introduction of catheters, guide wires, and other devices into the femoral artery for navigation to the site of a medical procedure such as a balloon angioplasty, stent implantation, or the like. After that procedure is performed, the medical devices are removed from the blood vessel 22, and the opening 24 formed in the blood vessel wall 26 must be closed. The apparatus 28 of FIG. 2 can be used to effectively provide such a closure.

Referring now to FIG. 2, the apparatus 28 is shown to include a delivery sheath 30 within which is provided an inner frame 32, an outer frame 34, and a universal joint 36 connecting the inner frame 32 and outer frame 34. It can be seen from FIG. 2 that the inner frame 32 and outer frame 34 and universal joint 36 can all be compressed to be held within the delivery sheath 30 during the insertion of the apparatus 28. This is referred to herein as the insertion configuration of the apparatus 28.

The inner frame 32 and outer frame 34 can be manufactured from any number of different materials but are particularly effective if manufactured from memory metals. Such memory metals are well known in the art and include the class of metals displaying both elasticity and the shape memory effect (SMA). Some suitable shape memory metals include, but are not limited to, nickel-titanium alloys (often marketed under the Nitinol™ trademark), and cobalt-chromium-nickel alloys (often marketed under the Elgiloy™ trademark). The use of such memory metals allows for the apparatus 28 to easily move from the insertion configuration of FIG. 2 to the deployed configuration of FIG. 5 as will be described in further detail herein. However, the teaching of this disclosure can be used to manufacture an apparatus made of conventional materials using springs, linkages, or other mechanical structures for compressing and expanding. Any strong and elastic material could be utilized, such as certain stainless steels or other materials not normally classified as "shape memory", and perhaps some components could be polymeric. Not all portions require elasticity, thus allowing some portions to be rigid, inelastic or plastic.

The universal joint connecting the inner frame 32 and outer frame 34 can be formed by any number of different structures enabling approximately 360° of motion along all three axes. In the depicted embodiment threads 35 and central ring 39 are used. Such threads may be formed by natural or synthetic fibers, polymers or memory metals. The universal joint is an important feature as well. As will be described and shown in further detail herein, it enables the inner frame 32 to pivot, rotate, and otherwise move relative to the outer frame 34 to most effectively align the apparatus 28 for closing the opening 24. This is particularly helpful in the event that the opening 24 is formed in a manner known in the medical arts as a "side-stick".

In explaining a "side-stick", it is helpful to refer to FIGS. 10a through 10d. As shown therein, the blood vessel 22 is depicted in top view having a longitudinal axis denoted by Greek letter α If the physician or other medical technician is able to successfully form the opening 24 such that the longitudinal axis α travels directly through the middle of the opening 24, the opening 24 is referred to as a "top-stick", this is depicted in FIG. 10a. If, however, as is often the case, the physician or other medical technician is slightly off with the incision, the opening 24 may be formed to one side of the longitudinal axis α. Looking at FIG. 10b, if the opening is formed to the left of the longitudinal axis α, this is referred to as a "left-side stick", and if the opening is formed to the right of the longitudinal axis α, this is referred to as a "right-side stick".

Figure 4:
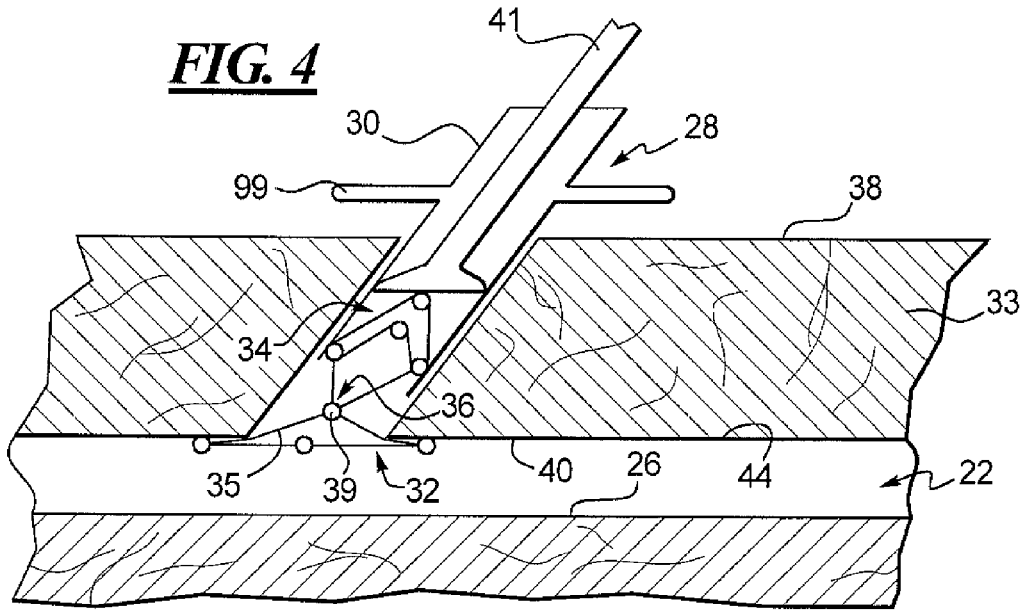
FIG. 4 is a cross-sectional view similar to FIG. 3, but with the inner frame deployed and pulled back into engagement with an interior surface of the blood vessel wall.

The type of "stick" is important to know in that as the blood vessel 22 is a substantially cylindrical shape, the opening will extend down and away from the physician if a side stick is formed. This is best depicted in the cross-sectional view of FIG. 10d, whereas the opening in a top-stick is relatively uniform and symmetrical as depicted in FIG. 10c. The shapes of these openings are even more complicated by the fact that the tissue tract 37 extending from the epidermal layer 38 through a subcutaneous layer 33 to the blood vessel wall 26 is often formed at an acute angle, typically 45°, to the longitudinal axis α. Given the various permutations of such compound angles, it is important that the device used to close the opening is able to pivot and move to accommodate such contours and orientations Referring now to FIG. 3, after the delivery sheath 30 is fully inserted into the tissue tract 37, the apparatus 28 can be extended from the delivery sheath 30 such that the inner frame 32 is free to expand into the deployed configuration shown in FIG. 3. Such extension can be accomplished through the use of a push or tamping rod 41. When the inner frame 32 is so deployed, it is fully within the blood vessel 22 but given its size does not substantially occlude blood flow therethrough. The physician can gauge the depth of delivery sheath 30 insertion by observing the position of optional circumferential flange 99 relative to the epidermal layer 38. Other indicia such as lines on the sheath can be used as well, or blood exits through a central channel In a next step depicted in FIG. 4, the entire delivery sheath and apparatus 28 are retracted through the tissue tract 37 such that the expanded inner frame 32 engages an inner surface 40 of a blood vessel wall 26. Once the inner frame 32 is so engaged with the blood vessel wall 26, the physician or other medical technician notices the resistance to further retraction thus knowing that the inner frame 32 is properly positioned.

Once the inner frame 32 is properly positioned, the outer frame 34 can be deployed as shown in FIG. 5 this may be accomplished again by retracting the delivery sheath 30 relative to the outer frame 34. The ram or push rod 41 may also be effective in accomplishing this motion. Once the outer frame 34 is free to expand into the deployed configuration, it obtains a position similar to the inner frame 32 but with its structure being deployed on an outer surface 44 of the blood vessel wall 26. As will be noted from FIG. 5, a retraction thread 46 is initially left in contact with the outer frame 34 in the event that the apparatus 28 is not properly located, the physician or other medical technician can then easily retract the entire apparatus 28 simply by pulling on the thread 46. To accomplish this removal in a controlled manner, the retraction thread interacts at control points on inner frame 32 such as by passing through loops or holes in inner frame 32 providing for effective collapsing of inner frame 32 as will be discussed below. However, assuming that the apparatus 28 is properly positioned, the thread 46 can be removed and a bandage 48 can be placed across an epidermal layer 38 of the patient to complete the procedure as shown in FIG. 6. In so doing, a mechanical seal is placed across the opening 24 and the blood vessel wall 26 thereby preventing blood flow from the blood vessel 22 and through the tissue tract 37, with both the tissue tract 37 and opening 24 being able to clot by natural thrombosis.

Referring now to FIG. 7, an alternative embodiment of the apparatus 28 is shown. It includes at least two additional features not depicted in FIGS. 1-6. In order to more fully seal the opening 26, a collagen plug or other gel-like substance such as, but not limited to, fibrin, PLA (polylactic acid), PLGA (poly(lactic-co-glycolic) acid), and PEG (polyethylene glycol), can be positioned between the inner frame 32 and outer frame 34. The biodegradable plug 52 is a malleable material or has a large enough clearance which can simply be placed around the universal joint and thus be held within the delivery sheath 30 as the apparatus is inserted into the tissue tract 37. Once the inner frame 32 is deployed and properly positioned against the inner surface of the blood vessel wall 26, the biodegradable plug is properly positioned directly at the opening 24 as well. The biodegradable plug 52 can extend outwardly in tissue tract 37 to further enhance sealing.

Another feature depicted in FIG. 7 is the inclusion of a covering 54. The covering 54 may be fabric or polymeric in nature and extends across the entire area of the inner and outer frames 32 and 34. As the inner and outer frames 32 and 34 are simply formed of a memory metal, the inclusion of a covering 54 presents a substantially opaque surface aiding in the full closure of the opening 24. In other embodiments not depicted but included in the scope of this disclosure, the apparatus 28 could have only the inner frame 32 covered or only the outer frame 34 covered.

Figure 9:
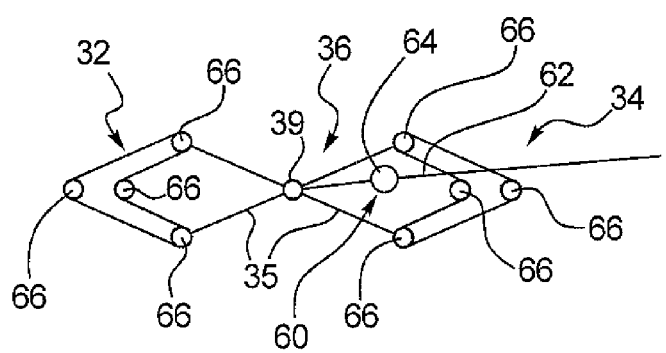
FIG. 9 is a schematic representation of another alternative embodiment including a mechanism for adjusting the distance between the inner and outer frames.

In certain instances, it may be necessary to adjust the distance between the inner frame 32 and outer frame 34. Accordingly, a mechanism for adjusting that distance can be provided as depicted in FIG. 9. As shown in FIG. 9, the inner frame 32 and outer frame 34 are still connected by universal joint 36 However, the adjustment mechanism enables the distance therebetween to be increased or decreased as needed. This can be accomplished by providing a cinch 60 formed by threads 62 and ring 64 forming a pulley arrangement enabling the physician or other medical technician to pull on thread 62 thereby drawing the inner frame 32 closer to the outer frame 34. This type of embodiment may be particularly helpful in the situation where the blood vessel wall 26 is of an unusually great or small thickness, or when the opening 24 is irregularly shaped. Such a cinch 60 may be provided with a one-way clutch (not shown) or the like to ensure once the proper spacing is attained, it is not lost.

Referring now to FIGS. 8a-8g, various shapes for the inner and outer frames 32 and 34 are depicted In the paragraphs that follow, the configurations will be referred to simply as the inner frame 32, but it should be understood that the shapes can be equally employed in conjunction with the outer frame 34 as well. In addition, while not depicted, it is also to be understood that the disclosure includes the possibility of providing inner and outer frames 32 and 34 which are of different shapes and sizes.

Figure 8E:
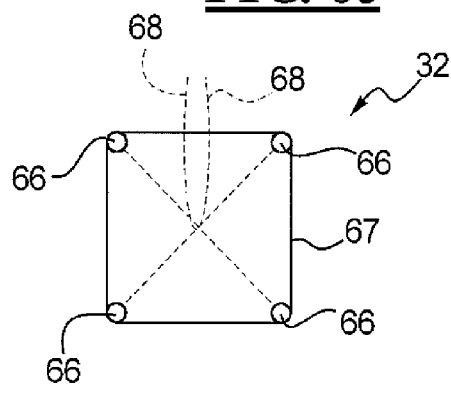
FIG. 8e is a plan view of an alternative embodiment of an inner frame in a rectangular configuration.
Figure 8F:
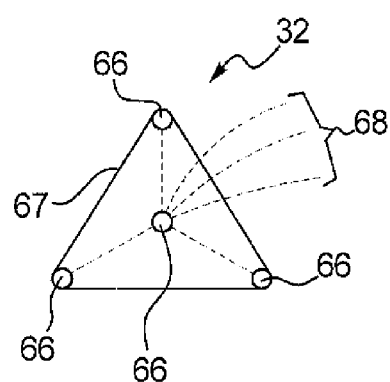
FIG. 8f is a plan view of an alternative embodiment of an inner frame in a triangular configuration.
Figure 8G:
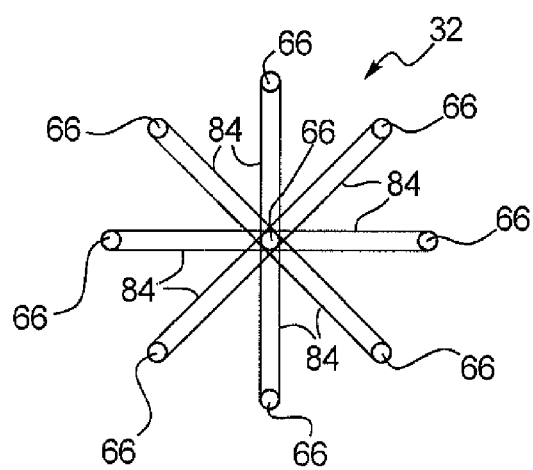
FIG. 8g is a plan view of another alternative embodiment of an inner frame in a star-shaped configuration.

With first reference to FIG. 8a, a circular configuration of the inner frame 32 is depicted. Such a circular configuration could be formed by the memory metal with multiple interior loops 66 being formed by the memory metal for attachment of retention threads 68. The memory metal may be formed with a perimeter 67 integral with the loops 66. In a similar embodiment depicted in FIG. 8b, again the inner frame 32 is of a generally circular configuration when deployed but only includes two loops 66 for the retention threads 68. In FIG. 5c, again an overall circular configuration is depicted but the inner frame 32 is divided into first and second halves 70 and 72 With respect to FIG. 8d, the inner frame 32 is depicted in a cloverleaf configuration with four individual rings 74, 76, 78 and 80 being joined by a central ring 82. In FIGS. 8e and 8f, rectangular and triangular configurations are depicted, respectively. Again, a plurality of loops 66 are provided for the retention threads 68. Finally, with respect to FIG. 8g, a star-shaped configuration is depicted having multiple arms 84 each having a loop 66 provided therein for the attachment of an adjustment thread (not shown) It is to be understood that the present disclosure can be used to manufacture inner and outer frames 32 and 34 of various other configurations not depicted and that the foregoing FIGS. 8a-8g are for exemplary purposes only. The threads may also provide a way of acutely removing the device if the physician is not completely satisfied with the result Referring now to FIG. 11, retention threads 68 are shown attached to loops 66. Loops 66, when pulled on by threads 68, cause the inner frame 32 to collapse thereby allowing the inner frame 32 to be retracted through sheath 30.

From the foregoing, it can be appreciated that the present disclosure sets forth an apparatus and method for closing arteriotomy sites or other openings in a blood vessel wall after a percutaneous medical procedure. The apparatus includes inner and outer frames preferably manufactured of memory metal and connected by a universal joint The manufacture of the frames from memory metals enables them to be compressed into a relatively small dimension, insertion configuration and housed within a delivery sheath. However, in other embodiments, memory metals need not be used, but rather conventional metals with conventional springs may be employed, or conventional mechanical deployment devices such as, but not limited to, umbrella-type actuators, may be employed In order to ensure the apparatus 28 remains in position after deployment, a suture or other mechanical mechanism can be used to secure the apparatus 28 For example, the suture could connect a proximal portion of the apparatus 28 to the subcutaneous tissue Once the delivery sheath is properly positioned proximate the arteriotomy site, the inner frame can be extended into the blood vessel and once freed from the confines of the delivery sheath, the inner frame can be expanded into its deployed configuration. The inner frame so deployed can then be retracted against the inner surface of the blood vessel wall for proper positioning. The delivery sheath can then be fully removed, enabling the outer frame to freely expand to its deployed configuration. Given the distance between the inner and outer frames, the blood vessel wall is sandwiched therebetween. If necessary, a synching mechanism can be used to ensure the proper distance between the frames and thus engagement of the blood vessel wall on both sides. A universal joint is used between the inner and outer frames to enable the frames to pivot and move relative thereto to facilitate closure of the generally cylindrical shape of the blood vessel while accommodating top-sticks and side-sticks In addition, the frames can be provided with a fabric or polymeric covering to facilitate and/or augment closure as well.

What is claimed is:

1. An apparatus for closing an opening in a blood vessel, comprising:
   a delivery catheter having a proximal end, a distal end, and a lumen extending therebetween;
   wherein the delivery catheter includes a circumferential flange disposed on an exterior surface thereof;
   a push rod slidably disposed within the lumen;
   an inner frame adapted to be positioned against an interior surface of a blood vessel wall;
   an outer frame adapted to be positioned against an exterior surface of a blood vessel wall; and
   a universal joint connecting the inner frame to the outer frame, the universal joint further including a pulley mechanism for adjusting the distance between the inner frame and outer frame;
   wherein the universal joint comprises a plurality of threads and a central ring disposed between the inner frame and the outer frame;
   wherein the central ring is axially spaced apart from the inner frame and the outer frame.

2. The apparatus of claim 1, wherein the inner frame and outer frame are made of a memory metal.

3. The apparatus of claim 2, wherein the memory metal is a nickel-titanium alloy.

4. The apparatus of claim 2, wherein the memory metal is a cobalt-chromium-nickel alloy.

5. The apparatus of claim 2, wherein at least one of the inner and outer frames further include a polymer covering.

6. The apparatus of claim 1, wherein the inner frame and outer frame are both compressible into an insertion configuration and expandable into a deployed configuration.

7. The apparatus of claim 6, wherein inner and outer frames have more than one lobe when in the deployed configuration.

8. The apparatus of claim 6, wherein the inner and outer frames have a generally circular configuration when in the deployed configuration with four smaller, inwardly directed loops about a circumference thereof.

9. The apparatus of claim 6, wherein the inner and outer frames are generally triangular when in the deployed configuration.

10. The apparatus of claim 6, wherein the inner and outer frames are generally rectangular when in the deployed configuration.

11. The apparatus of claim 6, wherein the inner and outer frames are generally star-shaped when in the deployed configuration.

12. The apparatus of claim 6, wherein the plurality of threads allow for movement between the deployed configuration and the insertion configuration.

13. The apparatus of claim 6, wherein the inner frame and outer frame are held in the insertion configuration when within the delivery catheter.

14. The apparatus of claim 6, wherein the inner and outer frames include first and second halves when in the deployed configuration.

15. The apparatus of claim 1, wherein the inner and outer frames are independently deployable.

16. The apparatus of claim 1, further including a biodegradable plug between the inner and outer frames.

17. The apparatus of claim 16, wherein the biodegradable plug is made of collagen.

18. The apparatus of claim 16, wherein the biodegradable plug is made of Fibrin.

19. The apparatus of claim 16, wherein the biodegradable plug is made of polylactic acid.

20. The apparatus of claim 16, wherein the biodegradable plug is made of poly(lactic-co-glycolic) acid.

21. The apparatus of claim 16, wherein the biodegradable plug is made of polyethylene glycol.

22. The apparatus of claim 1, wherein the mechanism for adjusting the distance between the inner and outer frames includes a cinch.

23. The apparatus of claim 1, wherein the inner frame and outer frame are made of stainless steel.

24. An apparatus for closing an opening in a blood vessel, comprising:
- a delivery catheter having a proximal end, a distal end, and a lumen extending therebetween;
- wherein the delivery catheter includes a circumferential flange disposed on an exterior surface thereof;
- a push rod slidably disposed within the lumen;
- an inner frame made of memory metal, the inner frame being compressible into an insertion configuration and expandable into a deployed configuration, the inner frame having a width greater than the width of the opening when deployed and a width smaller than the width of the opening when inserted, the inner frame having a polymer covering connected thereto;
- an outer frame made of memory metal, the outer frame being compressible into an insertion configuration and expandable into a deployed configuration, the outer frame having a width greater than the width of the opening when deployed and a width smaller than the width of the opening when inserted, the outer frame having a polymer covering connected thereto;
- a universal joint connecting the inner and outer frames, the universal joint being made of thread cooperating with a central ring and allowing multi-directional pivoting between the inner and outer frames;
- a biodegradable plug positioned between the inner and outer frames and around the universal joint; and
- the delivery catheter having the inner and outer frames disposed within the lumen thereof in their respective insertion configurations such that the inner frame is disposed distal of the outer frame;
- wherein the inner frame and the outer frame each define a proximal end and a distal end when disposed within the delivery catheter in their respective insertion configurations;
- wherein when the inner frame is moved from the insertion configuration to the deployed configuration, the proximal end expands outwardly;
- wherein when the outer frame is moved from the insertion configuration to the deployed configuration, the distal end expands outwardly;
- wherein the central ring is spaced apart from the inner frame and the outer frame.

* * * * *